US009696281B2

(12) United States Patent
Decitre

(10) Patent No.: US 9,696,281 B2
(45) Date of Patent: Jul. 4, 2017

(54) INSPECTION HEAD OF AN EDDY CURRENT NON-DESTRUCTIVE TESTING SENSOR AND SENSOR COMPRISING SUCH AN INSPECTION HEAD

(71) Applicant: COMMISSARIAT A L'ENERGIE ATOMIQUE ET AUX ENERGIES ALTERNATIVES, Paris (FR)

(72) Inventor: Jean-Marc Decitre, Marcoussis (FR)

(73) Assignee: Commissariat à l'énergie atomique et aux énergies alternatives, Paris (FR)

(*) Notice: Subject to any disclaimer, the term of this patent is extended or adjusted under 35 U.S.C. 154(b) by 56 days.

(21) Appl. No.: 14/890,359

(22) PCT Filed: May 6, 2014

(86) PCT No.: PCT/FR2014/051060
§ 371 (c)(1),
(2) Date: Nov. 10, 2015

(87) PCT Pub. No.: WO2014/181061
PCT Pub. Date: Nov. 13, 2014

(65) Prior Publication Data
US 2016/0109408 A1    Apr. 21, 2016

(30) Foreign Application Priority Data

May 10, 2013 (FR) ...................... 13 54218

(51) Int. Cl.
G01N 27/90    (2006.01)
(52) U.S. Cl.
CPC ....... *G01N 27/9093* (2013.01); *G01N 27/904* (2013.01); *G01N 27/9033* (2013.01)
(58) Field of Classification Search
CPC ........... G01N 27/9093; G01N 27/9033; G01N 27/904
See application file for complete search history.

(56) References Cited

U.S. PATENT DOCUMENTS 3,875,502 A    4/1975 Neumaier
5,659,248 A    8/1997 Hedengren et al.
(Continued)

FOREIGN PATENT DOCUMENTS

EP    2 037 261    3/2009
FR    2 904 693    2/2008
(Continued)

OTHER PUBLICATIONS

International Search Report Issued Jul. 18, 2014 in PCT/FR2014/051060 filed May 6, 2014.
(Continued)

*Primary Examiner* — David M Gray
*Assistant Examiner* — Michael Harrison
(74) *Attorney, Agent, or Firm* — Oblon, McClelland, Maier & Neustadt, L.L.P.

(57) ABSTRACT

An inspection head of an eddy current non-destructive testing sensor with separate transmitting and receiving functions includes a support whereon is arranged at least one transmitting/receiving element. Each element includes a circuit transmitting a local electromagnetic field, by circulating a predefined alternating current in the circuit, and an electromagnetic receiver sensitive to the locally transmitted electromagnetic field. The transmitting circuit is a portion of conductive sheet extending over a layer of the support layer in a predefined main direction of flow of the alternating current. The electromagnetic receiver is disposed facing the transmitting circuit relative to an axis normal to the layer of the support on which the portion of sheet extends to have an electromagnetic detection axis orthogonal to this normal axis and orthogonal to the predefined main direction of flow of the alternating current in the portion of conductive sheet.

10 Claims, 6 Drawing Sheets

(56) References Cited

U.S. PATENT DOCUMENTS

Figure 1:
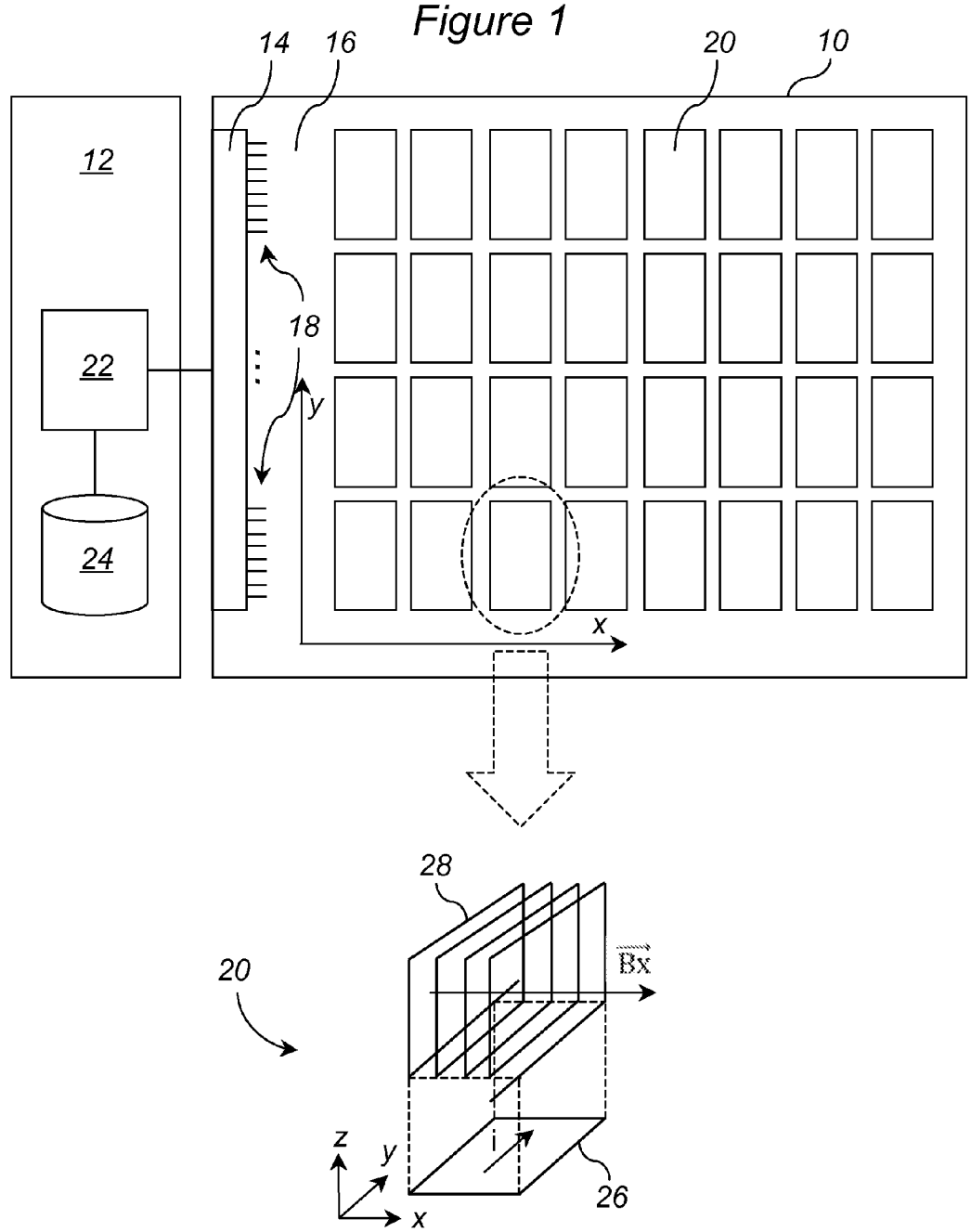

| | | | | |
|---|---|---|---|---|
| 6,150,809 A * | 11/2000 | Tiernan | ............... | G01N 27/82 |
| | | | | 324/225 |
| 6,914,427 B2 * | 7/2005 | Gifford | ............... | G01N 27/904 |
| | | | | 324/240 |
| 2005/0007108 A1 | 1/2005 | Dogaru | | |
| 2009/0091318 A1 | 4/2009 | Lepage et al. | | |
| 2010/0109658 A1 | 5/2010 | Decitre | | |
| 2012/0019236 A1 | 1/2012 | Tiernan et al. | | |
| 2016/0349213 A1 * | 12/2016 | Kollgaard | ............... | G01N 29/44 |

FOREIGN PATENT DOCUMENTS

| | | |
|---|---|---|
| WO | 2008 015195 | 2/2008 |
| WO | 2012 018541 | 2/2012 |

OTHER PUBLICATIONS

French Search Report Issued Oct. 24, 2013 in French Patent Application No. 1354218 filed May 10, 2013.

* cited by examiner

INSPECTION HEAD OF AN EDDY CURRENT NON-DESTRUCTIVE TESTING SENSOR AND SENSOR COMPRISING SUCH AN INSPECTION HEAD

This invention relates to an inspection head of an eddy current non-destructive testing sensor and sensor comprising such an inspection head.

A non-destructive testing sensor of this type uses the electromagnetic property of eddy currents for detecting defects such as scoring, cracks or corrosion in conductive structures of low thickness, not necessarily plane, such as aeronautical or nuclear metal parts. For example, this technology allows for the inspection of steam generator tubes in nuclear power plants.

An inspection head of such a sensor generally comprises at least one transmitting function circuit powered with alternating current in order to generate a local electromagnetic field and at least one receiver that is sensitive to this electromagnetic field. The electromagnetic receiver is often constituted of a receiving coil at the terminals of which an electromotive force of the same frequency as that of the alternating current power supply is induced. More precisely, when the inspection head of the eddy current non-destructive testing sensor is arranged in the vicinity of a part to be inspected, the transmitting circuit is supplied with a sinusoidal signal. An electromagnetic field of the same frequency is then transmitted in the air and in the part to be inspected. This results, at the terminals of the receiving coil, in a induced electromotive force that comes, on the one hand, from the coupling between the transmitting circuit and the receiving coil (with this coupling being modified in the presence of the part) and, on the other hand, from the magnetic field radiated by the induced currents in the part and which reveals the possible presence of a defect in the latter. The portion of the induced electromotive force coming from the magnetic field radiated by the presence of the possible defect constitutes the useful signal of the total induced electromotive force.

The invention applies more particularly to an inspection head of an eddy current non-destructive testing sensor with separate transmitting and receiving functions, i.e. an inspection head comprising a support whereon is arranged at least one transmitting/receiving element, with each transmitting/receiving element comprising:
- a circuit transmitting a local electromagnetic field by circulating a predefined alternating current in this circuit, and
- an electromagnetic receiver sensitive to the locally transmitted electromagnetic field, with this transmitting circuit and this electromagnetic receiver being separate devices.

In the case of an inspection head with a single transmitting/receiving element, it is necessary to displace the sensor along two main axes in order to obtain the two-dimensional mapping of a zone to be inspected of a conductive structure. As this displacement must further have a certain precision, it requires an expensive mechanical test bench able to provide the current position according to the two axes of displacement. In these conditions, the inspection of the conductive structure is not only complex but in addition very slow.

It is therefore advantageous to multiply the transmitting/receiving elements in one or several directions on the support of the inspection head in such a way as to limit such a displacement of the sensor. But, generally, a transmitting/receiving element of an eddy current non-destructive testing sensor has an encumbrance that is largely greater than the surface of the zone that it can inspect in the conductive structure. What can be qualified as the "useful surface" of the element is then limited. A minimum spacing between transmitting/receiving elements must further sometimes be respected according to the shape of the elements in order to provide a good operation of the whole and detect all of the defects. As such, it is not simple to have the transmitting/receiving elements on the support in such a way as to allow for an inspection without a shadow zone of the conductive structure. For example, in an embodiment of international patent application WO 2012/018541 A1 shown in FIG. 7 of this document, several transmitting/receiving elements with separate transmitting coils and receiving coils are aligned in a one-dimensional bar and connected in series in order to allow for several simultaneous inspections of zones in one dimension. But in this configuration, it is not possible to obtain the detection of an element independently of the others since the transmitting and receiving coils are placed in series in the same way. Furthermore, the elements are separated from one another in such a way that they do not make it possible to inspect without displacement the entire zone covered by the bar. As such, not only a displacement of the bar along an axis orthogonal to its main axis is required, but also a displacement along its main axis in order to cover the shadow zones.

A solution is proposed in the patent published under number FR 2 904 693 B1. This solution consists in arranging several lines of transmitting/receiving elements in the same one-dimensional inspection bar, with each line starting from the second being offset from the preceding one in such a way as to arrange the transmitting/receiving elements in staggered fashion. This disposition in staggered fashion compensates the low useful surface of the elements and allows for a complete covering in the main axis of the bar when the latter is displaced only orthogonally to this main axis. A mechanical encoder can then be used to automatically shift the lines between them during the display of the zone swept by the sensor and as such compensate for the staggering effect of the elements on the support. The displacement of the inspection head is therefore limited but not suppressed.

Another solution, proposed in the patent published under number U.S. Pat. No. 5,659,248, consists in arranging the transmitting/receiving elements in several layers of matrices of these elements, with the latter being arranged in staggered fashion from one layer to the next, again in order to compensate for their low useful surface. This three-dimensional configuration suppresses all shadow zones without requiring any displacement of the inspection head of the sensor, but at the price of a certain complexity since several layers of superimposed matrices of transmitting/receiving elements must be provided. Furthermore, due to the fact that all of the elements are not at the same distance from the surface to be inspected, the corrections to be provided in order to compensate the differences in air gap from one layer to the next singularly complicate the data processing.

It can then be desired to provide an inspection head of an eddy current non-destructive testing sensor that makes it possible to overcome at least part of the aforementioned problems and constraints.

An inspection head of an eddy current non-destructive testing sensor with separate transmitting and receiving functions is therefore proposed comprising a support whereon is arranged at least one transmitting/receiving element, with each transmitting/receiving element comprising:

a circuit transmitting a local electromagnetic field by circulating a predefined alternating current in this circuit, and an electromagnetic receiver sensitive to the locally transmitted electromagnetic field, wherein:

the transmitting circuit is a portion of conductive sheet extending over a layer of the support in a predefined main direction of flow of the alternating current, and the electromagnetic receiver is arranged:

opposite the transmitting circuit relative to an axis normal to the layer of the support on which said portion of sheet extends, and in such a way as to have an electromagnetic detection axis orthogonal to this normal axis and orthogonal to the predefined main direction of flow of the alternating current in the portion of conductive sheet.

As such, by combining a transmitting circuit in the form of a portion of a sheet with a predefined main direction of flow of the inductor current and an electromagnetic receiver arranged and oriented in such a way as to have a detection axis that is not only orthogonal to the normal but also orthogonal to the main direction of flow of the inductor current, a transmitting/receiving element with a high useful surface can be obtained. Indeed, it has been observed that this arrangement and this orientation of the receiver with respect to the transmitter make it possible to obtain a signal for detecting defects that has a unipolarity property. This leads to a non-zero response of the transmitting/receiving element on a possible defect in the conductive structure inspected and over its entire extent. By arranging the receiver opposite the transmitter according to this arrangement and this orientation, this results in reduced encumbrance at a given useful surface. This type of transmitting/receiving element thus becomes particularly adapted to a two-dimensional arrangement of such elements on the support of the inspection head for the design of a static two-dimensional detection sensor.

Optionally, each portion of the sheet forming the transmitting circuit is of rectangular surface and the normal projection of each electromagnetic receiver on the portion of sheet opposite of which it is arranged covers this rectangular surface. As such, the useful surface practically corresponds to the encumbrance of the transmitting/receiving element.

Also optionally, an inspection head according to the invention can comprise several transmitting/receiving elements arranged side by side in at least one main direction of the support. A static one- or two-dimensional detection is as such made possible.

Also optionally, the transmitting/receiving elements are arranged in a matrix in two main directions, with the first of the two main directions corresponding to that of the flow of the current in each portion of sheet and the transmitting/receiving elements being aligned in this first direction in such a way as to form several columns of the matrix, with the second of the two main directions corresponding to that of the electromagnetic detection axis of each electromagnetic receiver and the transmitting/receiving elements being arranged in staggered fashion in this second direction in such a way as to form several lines of the matrix. This particular configuration allows for a two-dimensional static detection with highly reduced and even non-existent shadow zones.

Also optionally, the portions of sheets of the same column of the matrix of transmitting/receiving elements are connected in series between them in such a way as to form a single conductive sheet that forms a matrix column opposite which are arranged several electromagnetic receivers.

Also optionally, the portion of sheet of each transmitting/receiving element is comprised of several conductor wires with the same current arranged in parallel in the predefined main direction of flow of this current.

Also optionally, the conductive sheets forming matrix columns are connected two by two as transmitting coils of which the spires comprise the conductor wires of these conductive sheets, with two conductive sheets connected together being spaced by at least one other conductive sheet.

Also optionally, the electromagnetic receiver of each transmitting/receiving element is a coil with spires of rectangular shape interlaced between the conductor wires of the portion of conductive sheet opposite which it is arranged.

Also optionally, the support comprises several layers of polyimide flexible film.

An eddy current non-destructive testing sensor is also proposed comprising:

an inspection head with at least one transmitting/receiving element such as defined hereinabove, a modulation/demodulation module for processing data intended for and coming from the inspection head, and a connector, arranged on the support of the inspection head, electrically connecting connection pathways from the support to the processing module, with the connection pathways being electrically connected to said at least one transmitting/receiving element.

Figure 2:
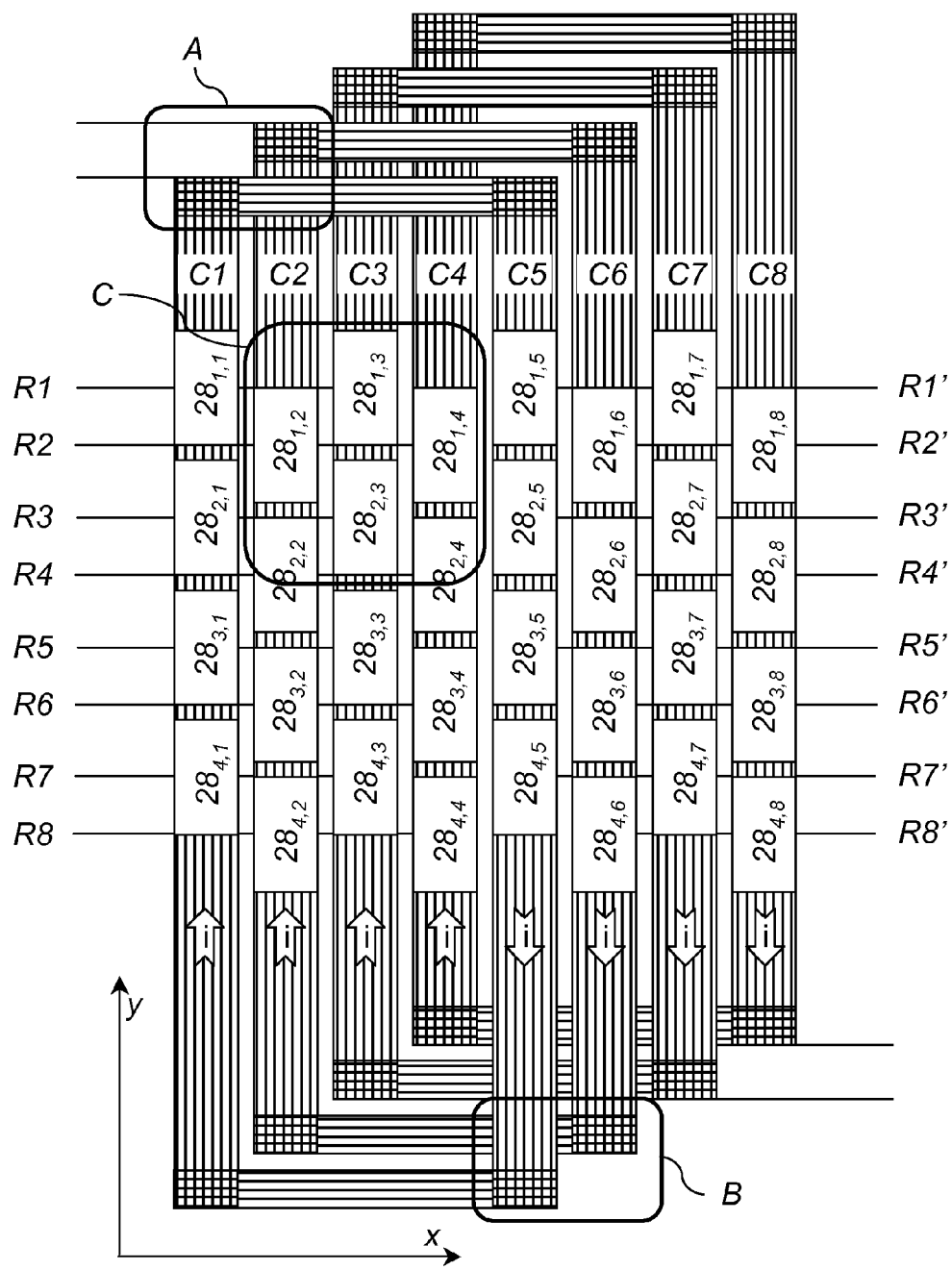
Figure 3A:
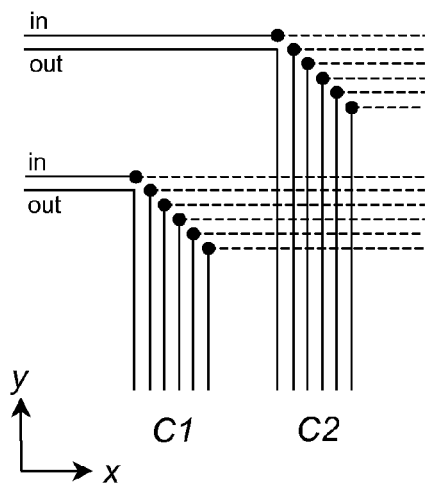
Figure 3B:
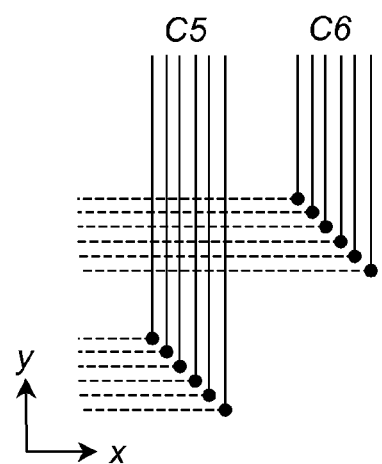
Figure 3C:
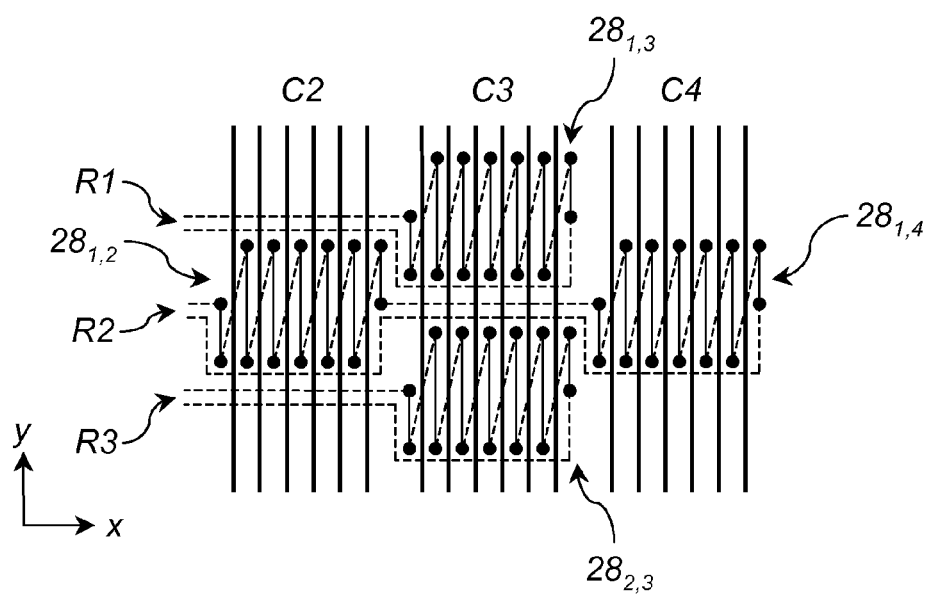
Figure 4:
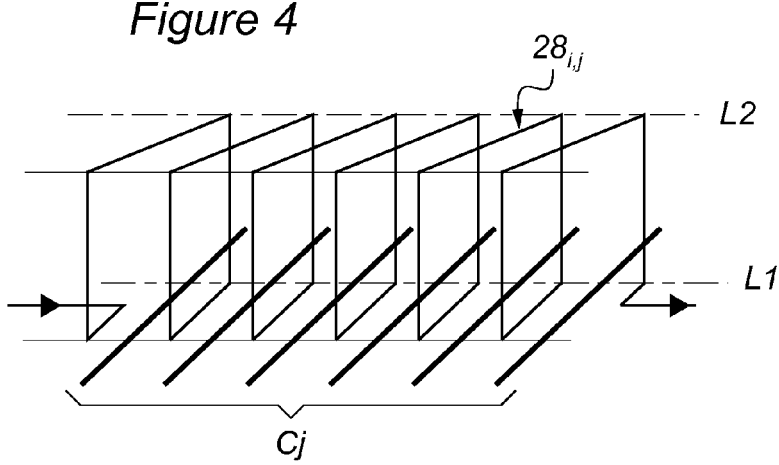
Figure 5:
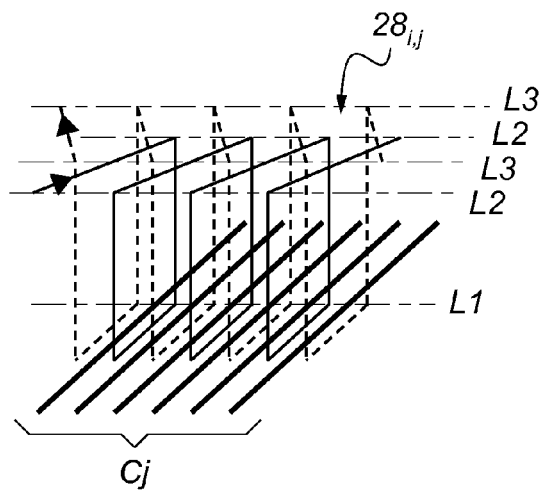
Figure 6:
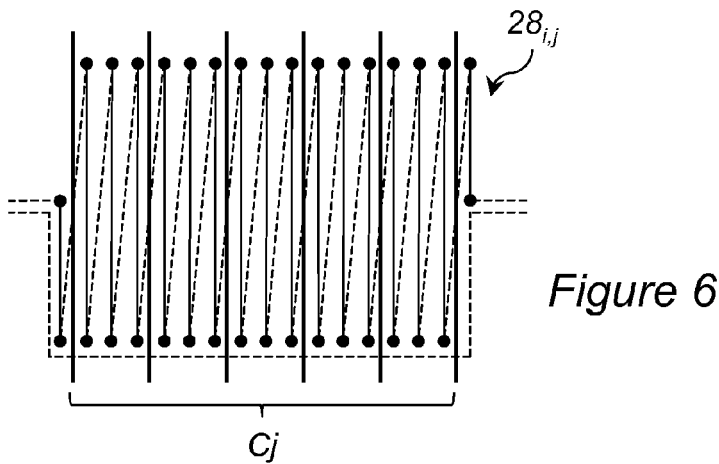
Figure 7:
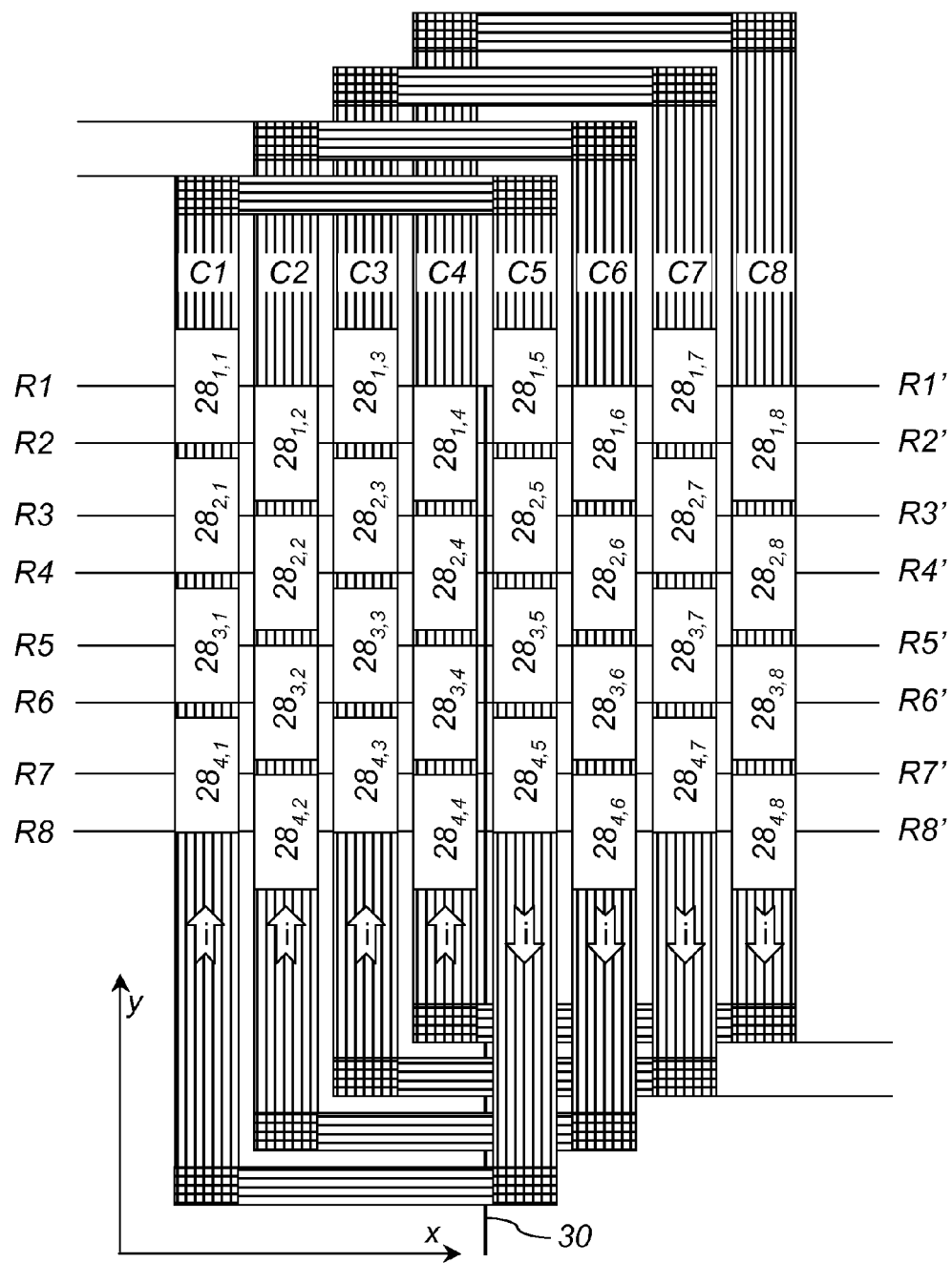
Figure 8B:
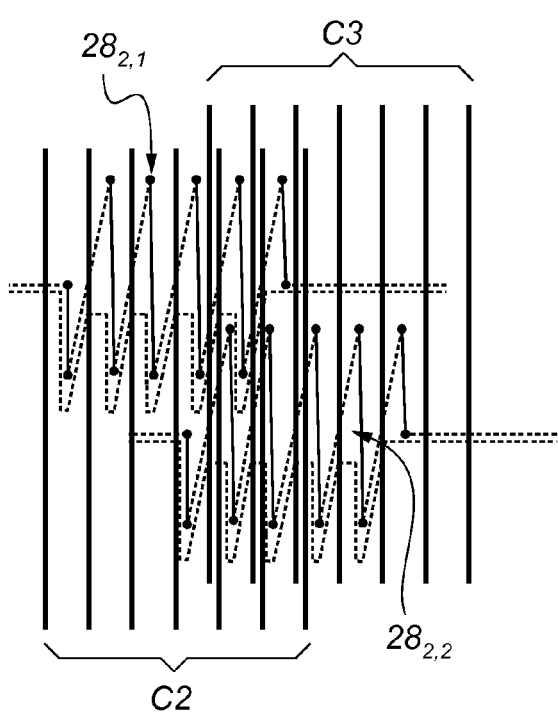
Figure 8A:
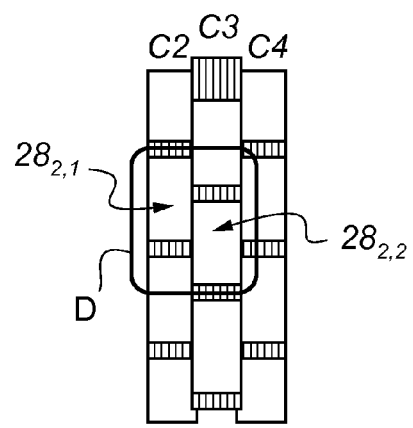

The invention shall be better understood when reading the following description, provided solely by way of example and made in reference to the annexed drawings wherein:

FIG. 1 diagrammatically shows the general structure of an eddy current non-destructive testing sensor, according to an embodiment of the invention, FIG. 2 diagrammatically shows and as a top view the general structure of an inspection head of the sensor of FIG. 1, according to an embodiment of the invention, FIGS. 3A, 3B and 3C diagrammatically show and as a top view details of the inspection head of FIG. 2, FIGS. 4, 5 and 6 diagrammatically show, in perspective for FIGS. 4 and 5, as a top view for FIG. 6, different alternative embodiments of a transmitting/receiving element of the inspection head of FIG. 2, FIG. 7 diagrammatically shows a first alternative embodiment of the inspection head of FIG. 2, and FIGS. 8A and 8B diagrammatically show a detail of a second alternative embodiment of the inspection head of FIG. 2.

The eddy current non-destructive testing sensor diagrammatically shown in FIG. 1 comprises an inspection head 10, a modulation/demodulation module 12 for processing data intended for and coming from the inspection head 10 and a connector 14, arranged on a support 16 of the inspection head 10. The connector 14 electrically connects connection pathways 18 from the support 16 to the processing module 12.

The inspection head 10 comprises several transmitting/receiving elements 20 distributed over the support 16 and connected to the connection pathways 18. In the example of FIG. 1, these elements 20 are distributed in a matrix along two main orthogonal axis x (axis of the lines) and y (axis of the columns) in such a way as to form a matrix of four lines and eight columns.

The processing module 12 such as diagrammatically shown in FIG. 1 comprises a processing unit 22 conventionally associated with a memory 24 (for example a RAM memory) and able to generate and process data intended for or coming from the transmitting/receiving elements 20, with this data being transmitted via the connector 14.

The processing unit 22 can for example be implemented in a computer device such as a conventional computer comprising a processor associated with one or several memories for the storage of data files and of computer programmes. The processing unit 22 can then be considered as being formed of a processor associated with a memory for storing instructions that it executes in the form of computer programmes. These computer programmes, or functions of the same computer programme, are able to modulate and possibly multiplex control signals intended to control the transmitting functions of the electromagnetic fields of the elements 20 in an independent and synchronised manner. They are also able to possibly demultiplex, but at least able to demodulate and process detection signals coming from induced eddy current receiving functions of element 20 also in an independent and synchronised manner. They could also be at least partially microprogrammed or microwired in dedicated integrated circuits. As such, as an alternative, the computer device implementing the processing unit 22 could be replaced with an electronic device comprised solely of digital circuits (without a computer programme) for carrying out of the same actions. The multiplexing/demultiplexing function is optional in the processing module 12 because the transmitting/receiving elements 20 can be organised topologically in order to be able to be solicited/interrogated independently of one another without requiring multiplexing. The operation of the processing unit 22 is well known to those skilled in the art and no further details will be provided.

The support 16 is advantageously a flexible support that allows the matrix of transmitting/receiving elements 20 to adapt to the relief of the regular surface of any conductive structure intended to be inspected par the eddy current non-destructive testing sensor of FIG. 1. It can comprise several layers of polyimide flexible film, for example Kapton (registered trademark), on or through which are arranged the elements that constitute the transmitting/receiving elements 20 and connection pathways 18. As such, the inspection head 10 is flexible and provides a constant air gap (i.e. distance between the inspected surface and the transmitting/receiving elements 20).

Each transmitting/receiving element 20 arranged on the support 16 of the inspection head 10 has separate transmitting and receiving functions. It comprises for this:

a transmitter circuit 26 of a local electromagnetic field $\vec{B}$ by circulation of a predetermined alternating current i in this circuit, and an electromagnetic receiver 28 sensitive to the locally transmitted electromagnetic field $\vec{B}$.

More precisely, the transmitting circuit 26 is a portion of conductive sheet extending over a layer of the support 16 in a predefined main direction of flow of the alternating current i. This predefined main direction is that of the axis y of the eight columns in the example shown. More precisely also and optionally, the portion of conductive sheet 26 is of rectangular surface oriented according to the directions of the two axes x and y.

The electromagnetic receiver 28 is for example a receiving coil arranged opposite the portion of conductive sheet 26 relative to an axis normal to the layer of the support 16 on which said portion of sheet 26 extends. This normal axis is therefore the axis z orthogonal to x and y. The receiving coil 28 is moreover constituted of a certain number of spires wound around an electromagnetic detection axis parallel to the axis x, i.e. orthogonal to the normal axis z and to the axis y of the predefined main direction of flow of the alternating current i in the portion of conductive sheet 26. In light of its arrangement around the axis x, the receiving coil 28 cannot be arranged on a single layer of the support 16, but on at least two separate layers and in its thickness. In this thickness, it can be arranged over, under or on either side of the conductive sheet 26. It is sensitive to a component $\vec{B}x$ of the locally-transmitted homogenous electromagnetic field.

It results from this configuration that the transmitting/receiving element 20 of FIG. 1 has a high useful surface contrary to the transmitting/receiving elements that are generally known, due to the unipolarity of the defect detection signal that it supplies. More precisely, it is experimentally shown that the response provided by the receiving coil 28 of any transmitting/receiving element to an excitation of the corresponding portion of conductive sheet 26 has the following characteristics:

its unipolarity leads to a non-zero signal shape over the entire extent of a defect, it can be negative, but only over a highly limited zone, which prevents the possible cancellation of the response when two defects are adjacent and which can be detected by several neighbouring transmitting/receiving elements, its shape is close to that of the rectangular function over the entire surface of the transmitting/receiving element and even has a net level of low rippling for defects with a length that exceeds a certain threshold, it is of a constant amplitude regardless of the length of the defect.

Further note that advantageously, the orthogonal projection of the receiving coil 28 in the plane (x, y) has an encumbrance corresponding to the rectangular surface of the portion of conductive sheet 26 by covering it. More precisely, the receiving coil 28 is constituted of rectangular spires over a length, along the axis y, equal to the dimension along the same axis of the portion of conductive sheet 26 and over a width, along the axis x, equal to the dimension along the same axis of the portion of conductive sheet 26. As such, the encumbrance of the transmitting/receiving element 20 corresponds precisely to its useful surface and it is possible to have several of these of this type, side by side, very close to one another and in a matrix, in order to constitute the inspection head 10. The eddy current non-destructive testing sensor of FIG. 1 is as such particularly adapted for the static inspection of two-dimensional zones of conductive structures, with these two-dimensional zones being of the same dimensions as the matrix of the transmitting/receiving elements 20. The flexibility of the support 16 further makes it possible to be adapted to adjusted surfaces that have a certain relief.

The more precise structure of the inspection head 10, shown diagrammatically in FIG. 1, shall now be described in reference to FIG. 2.

According to the embodiment shown in this figure, the transmitting/receiving elements 20 are aligned four by four along the axis y of the columns of the matrix that they constitute. They are furthermore arranged in staggered fashion eight by eight with a pitch of two along the axis x of the lines of the matrix. The disposition in staggered fashion is chosen in order to prevent shadow zones, but is not mandatory. Furthermore, the portions of sheets of the same column of the matrix of transmitting/receiving elements 20 are connected in series together in such a way as to form a single conductive sheet that forms a matrix column opposite which are arranged several receiving coils.

More precisely, four portions of sheets are connected in series in order to form a single conductive sheet C1 that forms the first column of the matrix parallel to the axis y. On this first column are arranged four receiving coils $28_{1,1}$, $28_{2,1}$, $28_{3,1}$ and $28_{4,1}$ with detection axes parallel to the axis x. Four other portions of sheets are connected in series in order to form a single conductive sheet C2 that forms the second column of the matrix parallel to the axis y. On this second column are arranged four receiving coils $28_{1,2}$, $28_{2,2}$, $28_{3,2}$ and $28_{4,2}$ with detection axes parallel to the axis x, in staggered fashion with respect to the receiving coils $28_{1,1}$, $28_{2,1}$, $28_{3,1}$ and $28_{4,1}$. Four other portions of sheets are connected in series in order to form a single conductive sheet C3 that forms the third column of the matrix parallel to the axis y. On this third column are arranged four receiving coils $28_{1,3}$, $28_{2,3}$, $28_{3,3}$ and $28_{4,3}$ with detection axes parallel to the axis x, in staggered fashion with respect to the receiving coils $28_{1,2}$, $28_{2,2}$, $28_{3,2}$ and $28_{4,2}$ in such a way as to be aligned along the axis x with the receiving coils $28_{1,1}$, $28_{2,1}$, $28_{3,1}$ and $28_{4,1}$. Four other portions of sheets are connected in series in order to form a single conductive sheet C4 that forms the fourth column of the matrix parallel to the axis y. On this fourth column are arranged four receiving coils $28_{1,4}$, $28_{2,4}$, $28_{3,4}$ and $28_{4,4}$ with detection axes parallel to the axis x, in staggered fashion with respect to the receiving coils $28_{1,3}$, $28_{2,3}$, $28_{3,3}$ and $28_{4,3}$ in such a way as to be aligned along the axis x with the receiving coils $28_{1,2}$, $28_{2,2}$, $28_{3,2}$ and $28_{4,2}$. Four other portions of sheets are connected in series in order to form a single conductive sheet C5 forming the fifth column of the matrix parallel to the axis y. On this fifth column are arranged four receiving coils $28_{1,5}$, $28_{2,5}$, $28_{3,5}$ and $28_{4,5}$ with detection axes parallel to the axis x, in staggered fashion with respect to the receiving coils $28_{1,4}$, $28_{2,4}$, $28_{3,4}$ and $28_{4,4}$ in such a way as to be aligned along the axis x with the receiving coils $28_{1,3}$, $28_{2,3}$, $28_{3,3}$ and $28_{4,3}$. Four other portions of sheets are connected in series in order to form a single conductive sheet C6 forming the sixth column of the matrix parallel to the axis y. On this sixth column are arranged four receiving coils $28_{1,6}$, $28_{2,6}$, $28_{3,6}$ and $28_{4,6}$ with detection axes parallel to the axis x, in staggered fashion with respect to the receiving coils $28_{1,5}$, $28_{2,5}$, $28_{3,5}$ and $28_{4,5}$ in such a way as to be aligned along the axis x with the receiving coils $28_{1,4}$, $28_{2,4}$, $28_{3,4}$ and $28_{4,4}$. Four other portions of sheets are connected in series in order to form a single conductive sheet C7 forming the seventh column of the matrix parallel to the axis y. On this seventh column are arranged four receiving coils $28_{1,7}$, $28_{2,7}$, $28_{3,7}$ and $28_{4,7}$ with detection axes parallel to the axis x, in staggered fashion with respect to the receiving coils $28_{1,6}$, $28_{2,6}$, $28_{3,6}$ and $28_{4,6}$ in such a way as to be aligned along the axis x with the receiving coils $28_{1,5}$, $28_{2,5}$, $28_{3,5}$ and $28_{4,5}$. Finally, four last portions of sheets are connected in series in order to form a single conductive sheet C8 forming the eighth and last column of the matrix parallel to the axis y. On this eighth column are arranged four receiving coils $28_{1,8}$, $28_{2,8}$, $28_{3,8}$ and $28_{4,8}$ with detection axes parallel to the axis x, in staggered fashion with respect to the receiving coils $28_{1,7}$, $28_{2,7}$, $28_{3,7}$ and $28_{4,7}$ in such a way as to be aligned along the axis x with the receiving coils $28_{1,6}$, $28_{2,6}$, $28_{3,6}$ and $28_{4,6}$.

In sum, the matrix of transmitting/receiving elements 20 is constituted of eight columns, formed by eight conductive sheets C1 to C8 parallel to one another, equally distant, close to one another and intended to be passed through by a current i with a direction along the axis y, and of four lines, in which of each of them are arranged in staggered fashion, opposite the eight conductive sheets according to the axis z, eight receiving coils with detection axes oriented along the axis x, in such a way as to form thirty-two transmitting/receiving elements 20.

In addition, the receiving coils are connected in series two by two, advantageously along the axis x, in order to reduce the number of supply wires as much as possible. This putting into series is done with a pitch of two in order to prevent any coupling between adjacent conductive sheets and receiving coils.

As such, on the first line of the matrix:
the receiving coils $28_{1,1}$ and $28_{1,3}$ are connected in series to an acquisition output R1 to the left of the matrix,
the receiving coils $28_{1,5}$ and $28_{1,7}$ are connected in series to an acquisition output R1' to the right of the matrix,
the receiving coils $28_{1,2}$ and $28_{1,4}$ are connected in series to an acquisition output R2 to the left of the matrix, and
the receiving coils $28_{1,6}$ and $28_{1,8}$ are connected in series to an acquisition output R2' to the right of the matrix.

On the second line of the matrix:
the receiving coils $28_{2,1}$ and $28_{2,3}$ are connected in series to an acquisition output R3 to the left of the matrix,
the receiving coils $28_{2,5}$ and $28_{2,7}$ are connected in series to an acquisition output R3' to the right of the matrix,
the receiving coils $28_{2,2}$ and $28_{2,4}$ are connected in series to an acquisition output R4 to the left of the matrix, and
the receiving coils $28_{2,6}$ and $28_{2,8}$ are connected in series to an acquisition output R4' to the right of the matrix.

On the third line of the matrix:
the receiving coils $28_{3,1}$ and $28_{3,3}$ are connected in series to an acquisition output R5 to the left of the matrix,
the receiving coils $28_{3,5}$ and $28_{3,7}$ are connected in series to an acquisition output R5' to the right of the matrix,
the receiving coils $28_{3,2}$ and $28_{3,4}$ are connected in series to an acquisition output R6 to the left of the matrix, and
the receiving coils $28_{3,6}$ and $28_{3,8}$ are connected in series to an acquisition output R6' to the right of the matrix.

On the fourth line of the matrix:
the receiving coils $28_{4,1}$ and $28_{4,3}$ are connected in series to an acquisition output R7 to the left of the matrix,
the receiving coils $28_{4,5}$ and $28_{4,7}$ are connected in series to an acquisition output R7' to the right of the matrix,
the receiving coils $28_{4,2}$ and $28_{4,4}$ are connected in series to an acquisition output R8 to the left of the matrix, and
the receiving coils $28_{4,6}$ and $28_{4,8}$ are connected in series to an acquisition output R8' to the right of the matrix.

Furthermore, the conductive sheets C1 to C8 are all comprised of several conductor wires with the same current i arranged in parallel along the axis y and are connected two by two as four rectangular transmitting coils, with two conductive sheets connected together being spaced by at least one other conductive sheet in order to avoid any coupling between adjacent conductive sheets. In the plane of FIG. 2, the conductive sheets connected together are spaced from three other conductive sheets. More precisely, the sheets C1 and C5 are connected together and electrically powered (with current i) at the top left of the matrix, sheets C2 and C6 are connected together and electrically powered (with current i) at the top left of the matrix, sheets C3 and C7 are connected together and electrically powered (with current i) at the bottom right of the matrix, sheets C4 and C8 are connected together and electrically powered (with current i) at the bottom right of the matrix.

As such, in order to acquire the detection signals from each one of the receiving coils, the following transmissions/receivings should be carried out:

supplying, at the top left of the matrix, the first transmitting coil comprised of the conductive sheets C1 and C5 connected together and acquiring the signals on the outputs R1, R3, R5, R7, R1', R3', R5' and R7' in order to have the responses of the receiving coils $28_{1,1}$, $28_{2,1}$, $28_{3,1}$, $28_{4,1}$, $28_{1,5}$, $28_{2,5}$, $28_{3,5}$ and $28_{4,5}$, supplying, at the top left of the matrix, the second transmitting coil comprised of the conductive sheets C2 and C6 connected together and acquiring the signals on the outputs R2, R4, R6, R8, R2', R4', R6' and R8' in order to have the responses of the receiving coils $28_{1,2}$, $28_{2,2}$, $28_{3,2}$, $28_{4,2}$, $28_{1,6}$, $28_{2,6}$, $28_{3,6}$ and $28_{4,6}$, supplying, at the bottom right of the matrix, the third transmitting coil comprised of the conductive sheets C3 and C7 connected together and acquiring the signals on the outputs R1, R3, R5, R7, R1', R3', R5' and R7' in order to have the responses of the receiving coils $28_{1,3}$, $28_{2,3}$, $28_{3,3}$, $28_{4,3}$, $28_{1,7}$, $28_{2,7}$, $28_{3,7}$ and $28_{4,7}$, and supplying, at the bottom right of the matrix, the fourth transmitting coil comprised of the conductive sheets C4 and C8 connected together and acquiring the signals on the outputs R2, R4, R6, R8, R2', R4', R6' and R8' in order to have the responses of the receiving coils $28_{1,4}$, $28_{2,4}$, $28_{3,4}$, $28_{4,4}$, $28_{1,8}$, $28_{2,8}$, $28_{3,8}$ and $28_{4,8}$.

In light of the fact that two conductive sheets connected together are passed through by a current of the same intensity but of opposite directions, this can be offset by adjusting the direction of winding of the receiving coils.

With regards to the precise connection of the conductive sheets together, the detail A of FIG. 2 is shown precisely in FIG. 3A and the detail B of FIG. 2 is shown precisely in FIG. 3B. These details show that each transmitting coil constituted of two conductive sheets connected together comprises rectangular spires distributed over two layers of the support 16. The portions of spires along the axis y constituting the conductive sheets (C1 and C2 in FIG. 3A, C5 and C6 in FIG. 3B), shown as solid lines, are arranged on a first layer of the support 16 while the portions of spires along the axis x of connection between conductive sheets, shown as a dotted line, are arranged on a second layer of the support 16. The connection between the portions of spires of the first layer and those of the second layer is carried out by through-vias shown by black points in FIGS. 3A and 3B. The supply with current of each transmitting coil is done via an "in" connection for the arrival of the current i and an "out" connection for the output of the current i. In the topology of FIGS. 3A and 3B, it was chosen to connect one of the portions of the spire of each conductive sheet C5 and C6 to the "in" arrival and one of the portions of the spire of each conductive sheet C1 and C2 to the output "out".

With regards to the precise connection of the receiving coils together, the detail C of FIG. 2 is precisely shown in FIG. 3C. It shows in particular the receiving coils $28_{1,2}$, $28_{1,3}$, $28_{1,4}$ and $28_{2,3}$. These receiving coils are constituted of spires of rectangular shape and arranged in the thickness of the support 16. For each rectangular spire, a first portion shown as a thin solid line is arranged on the aforementioned first layer of the support 16, a second portion shows as a broken thin line is arranged on the aforementioned second layer of the support and two other portions connecting the first and second portions are constituted of through-vias between the two layers, with these through-vias shown by black points.

The interlacing of the spires of the receiving coils between the conductor wires of the conductive sheets is shown as a representation on FIG. 3C, as thick solid lines, of the conductive sheets C2, C3 and C4 arranged on the first layer of the support 16 with the first portions of spires of the receiving coils. The relative arrangement between a receiving coil $28_{i,j}$ of FIG. 3C and the conductor wires of the corresponding portion of conductive sheet Cj is more clearly shown in perspective in FIG. 4.

Note therefore that in accordance with the implementation shown in FIGS. 3C and 4 of the matrix of transmitting/receiving elements 20, the latter requires only two layers L1 and L2 connected together by through-vias. The support 16 can therefore be realised concretely from kapton (registered trademark) with two layers of copper. Also note that the receiving coils $28_{1,3}$, $28_{1,4}$ and $28_{2,3}$ are at the end of the line for the connections to the outputs R1, R2 and R3 in such a way that a return conductor wire at the outputs R1, R2 and R3 is provided in the second layer of the support 16. On the other hand, no return wire is provided for the receiving coil $28_{1,2}$, as the latter is not at the end of the line and being connected in series with the receiving coil $28_{1,4}$.

Alternatively and as shown in perspective in FIG. 5, the return conductor wire of a series of receiving coils can be used to form additional spires of these receiving coils also interlacing with the conductor wires of the conductive sheets. In this case, it is necessary to have three layers L1, L2 and L3 of support 16 so that the spires of the return path are not in contact with the spires of the outgoing path in a receiving coil $28_{i,j}$. This increases the sensitivity of the transmitting/receiving element.

As an alternative also and as shown as a top view in FIG. 6, the interlacing of the spires of a receiving coil $28_{i,j}$ with the conductor wires of the corresponding conductive sheet Cj can be designed to have several spires, three here, between each conductor wire of the conductive sheet. This also increases the sensitivity of the transmitting/receiving element.

FIG. 7 diagrammatically shows a slight alternative embodiment of the inspection head of FIG. 2. This alternative embodiment consists in providing an electrical earth 30 extending between the fourth C4 and fifth C5 conductive sheets. To this electrical earth 30 are connected all of the series of receiving coils connected to the outputs R1 to R8 and R1' to R8'. This alternative embodiment has the advantage of its simplicity in terms of electrical connections since no return wire is required. On the other hand, the performance of the testing sensor is slightly degraded because this simplification is carried out at the price of a measurement of the normal component of the electromagnetic field induced.

FIGS. 8A and 8B show an alternative embodiment according to which the conductive sheets C1 to C8 overlap partially in such a way that the receiving coils arranged in staggered fashion from one conductive sheet to the next also overlap partially. In this configuration, the density of the transmitting/receiving elements is increased and there is no longer any shadow zones as shown in FIG. 8A wherein are shown partially by way of example the conductive sheets C2, C3 and C4 and some of their receiving coils. The detail D surrounds in particular the zones occupied by the receiving coils $28_{2,1}$ and $28_{2,2}$. The FIG. 8B diagrammatically shows, for the detail D, the relative arrangement possible of the conductor wires of sheets and of spires of receiving coils as well as line return wires that make it possible to require only two layers of support 16 in order to carry out this configuration.

It clearly appears that an eddy current non-destructive testing sensor such as the one described hereinabove makes possible, thanks to the particular configuration of its transmitting/receiving elements which provides it with a high useful surface, a static two-dimensional inspection of structures without shadow zones. It is possible to detect therein all of the possible defects of a given orientation and of a length greater than a given length in the surface covered by the inspection head, and this, regardless of the position of these defects with respect to the transmitting/receiving elements. Furthermore, the identical matrix arrangement of the transmitting/receiving elements provides a constant air gap and therefore an identical sensitivity of the inspection head over its entire inspection surface regardless of the location of a defect.

Note moreover that the invention is not limited to the embodiments described hereinabove.

Using for example the teaching of the aforementioned documents, in particular patent documents FR 2 904 693 B1 and U.S. Pat. No. 5,659,248, it is possible to increase the density of the transmitting/receiving elements in order to reduce the minimum length of the defects that can be detected, by using a support with four or more layers. In particular, it is possible to arrange at a right angle two matrices of elements such as that shown in FIG. 2 on at least four layers of support in such a way as to be able to detect all of the possible defects regardless of their orientation.

Also as an alternative, it is possible to place ferrite cores in order to increase the sensitivity of the transmitting/receiving elements. Arranged on the external surface of the elements and in plane sheets, they make it possible to prevent the radiation of electromagnetic field in the air, to decrease the reluctance of the transmitting/receiving circuit and subsequently to increase the induced currents in the conductive structure to be inspected. Arranged in the thickness of the receiving coils, they make it possible to reduce their reluctance and to increase the sensitivity of the sensor.

Also as an alternative, the electromagnetic receivers of the transmitting/receiving elements have been considered in the form of receiving coils in the embodiments described hereinabove, but these receiving coils could be more generally replaced with other electromagnetic receivers, among which receivers of the GMR (Giant MagnetoResistance) type for example. It is sufficient that these electromagnetic receivers be arranged opposite the conductive sheets according to the axis z and in such a way as to have an electromagnetic detection axis along the axis x in order to be suitable in an inspection head according to the invention. GMR receivers do not contain spires. They can be arranged on the surface according to a stacking of nanometric layers of electromagnetic materials, indifferently over or under the conductive sheets. The presence of local electromagnetic fields generated by the circulation of inductor currents in the conductive sheets produces, in these GMR receivers, variations in resistances that can be detected in the form of variations in voltage when a current flows therein. It is therefore very simple to adapt the embodiments that were detailed hereinabove by replacing the receiving coils with such GMR receivers.

It will appear more generally to those skilled in the art that various modifications can be made to the embodiments described hereinabove, in light of the teaching that has just been disclosed. In the following claims, the terms used must not be interpreted as limiting the claims to the embodiments exposed in this description, but must be interpreted in order to include therein all of the equivalents that the claims aim to cover due to their formulation and of which foreseeing is within the scope of those skilled in the art by applying their general knowledge to the implementation of the teaching that has just been disclosed.

The invention claimed is:

1. An inspection head of an eddy current non-destructive testing sensor with separate transmitting and receiving functions, comprising:
a support whereon is arranged at least one transmitting/receiving element, with each transmitting/receiving element comprising:
a transmitting circuit transmitting a local electromagnetic field by circulating a predefined alternating current in the circuit, and
an electromagnetic receiver including an electromagnetic detection axis sensitive to the locally transmitted electromagnetic field,
wherein
the transmitting circuit is a portion of conductive sheet extending over a layer of the support in a predefined main direction of flow of the alternating current, and
the electromagnetic receiver is arranged:
opposite the transmitting circuit relative to an axis normal to the layer of the support on which the portion of sheet extends, and
such that its electromagnetic detection axis is orthogonal to the normal axis and orthogonal to the predefined main direction of flow of the alternating current in the portion of conductive sheet.

2. An inspection head according to claim 1, wherein each portion of the sheet forming a transmitting circuit is of rectangular surface and the normal projection of each electromagnetic receiver on the portion of sheet opposite which it is arranged covers this rectangular surface.

3. An inspection head according to claim 1, comprising plural transmitting/receiving elements arranged side by side in at least one main direction of the support.

4. An inspection head according to claim 3, wherein the transmitting/receiving elements are arranged in a matrix in two main directions, with the first of the two main directions corresponding to that of the flow of the current in each portion of sheet and the transmitting/receiving elements being aligned in the first direction to form plural columns of the matrix, with the second of the two main directions corresponding to that of the electromagnetic detection axis of each electromagnetic receiver and the transmitting/receiving elements being arranged in staggered fashion in the second direction to form plural lines of the matrix.

5. An inspection head according to claim 4, wherein the portions of sheets of the same column of the matrix of transmitting/receiving elements are connected in series between them to form a single conductive sheet that forms a matrix column opposite which are arranged plural electromagnetic receivers.

6. An inspection head according to claim 1, wherein the portion of sheet of each transmitting/receiving element is comprised of plural conductor wires with the same current arranged in parallel in the predefined main direction of flow of the current.

7. An inspection head according to claim 5, wherein the conductive sheets forming matrix columns are connected two by two as transmitting coils of which the spires comprise the conductor wires of the conductive sheets, with two conductive sheets connected together being spaced by at least one other conductive sheet.

8. An inspection head according to claim 6, wherein the electromagnetic receiver of each transmitting/receiving element is a coil with spires of rectangular shape interlaced between the conductor wires of the portion of conductive sheet opposite which it is arranged.

9. An inspection head according to claim 1, wherein the support comprises plural layers of polyimide flexible film.

10. An eddy current non-destructive testing sensor comprising:
 an inspection head comprising at least one transmitting/receiving element according to claim 1;
 a modulation/demodulation module for processing data intended for and coming from the inspection head; and
 a connector, arranged on the support of the inspection head, electrically connecting connection pathways from the support to the processing module, with the connection pathways being electrically connected to the at least one transmitting/receiving element.

* * * * *